(12) United States Patent
Nelson

(10) Patent No.: US 8,017,912 B1
(45) Date of Patent: Sep. 13, 2011

(54) SYSTEM AND METHOD FOR SPECTRAL-BASED PASSIVE THREAT WARNING

(75) Inventor: Richard J. Nelson, Brookline, NH (US)

(73) Assignee: Solid State Scientific Corporation, Hollis, NH (US)

( * ) Notice: Subject to any disclaimer, the term of this patent is extended or adjusted under 35 U.S.C. 154(b) by 1140 days.

(21) Appl. No.: 11/796,928

(22) Filed: Apr. 30, 2007

Related U.S. Application Data

(60) Provisional application No. 60/795,800, filed on Apr. 28, 2006.

(51) Int. Cl.
*G01J 5/02* (2006.01)
*G01K 11/30* (2006.01)
(52) U.S. Cl. .................... 250/340; 702/134; 702/135
(58) Field of Classification Search .............. 250/340, 250/369; 702/134, 135; 324/76.14
See application file for complete search history.

(56) References Cited

U.S. PATENT DOCUMENTS

2002/0175291 A1* 11/2002 Reeder et al. ............. 250/369
2005/0195086 A1* 9/2005 King ........................ 340/578
* cited by examiner

*Primary Examiner* — David Porta
*Assistant Examiner* — Carolyn Igyarto
(74) *Attorney, Agent, or Firm* — Louis J. Franco; Law Office of Louis J. Franco

(57) ABSTRACT

A method of classifying an electromagnetic-energy emitting source event as one of a first, second, and third class event includes registering an irradiance spectrum from the source event. The intensity of the energy emitted from the source event is measured within each of first, second and third energy sub-ranges and first, second and third relative-energy values are associated with, respectively, the first, second and third energy sub-ranges. A first class-eliminating determination is rendered by comparing to one another a first selected set of two of the relative-energy values, thereby yielding two remaining-candidate event classes. When necessary, a second class-eliminating determination renders the proper classification for the source event by comparing to one another a second selected set of relative-energy values including the relative-energy value not selected for inclusion in the first selected set of two relative-energy values and one of the previously selected relative-energy values. The energy-value comparisons are carried out with reference to modeled source-event irradiance data from which expected ratio behaviors among the selected energy sub-ranges are ascertainable relative particular event types at various ranges and under disparate atmospheric conditions.

15 Claims, 8 Drawing Sheets

Graphical representation of spectral irradiance data included in an illustrative modeled spectral data set 235 that is "pre-stored" in computer memory 215, as shown in FIG. 1

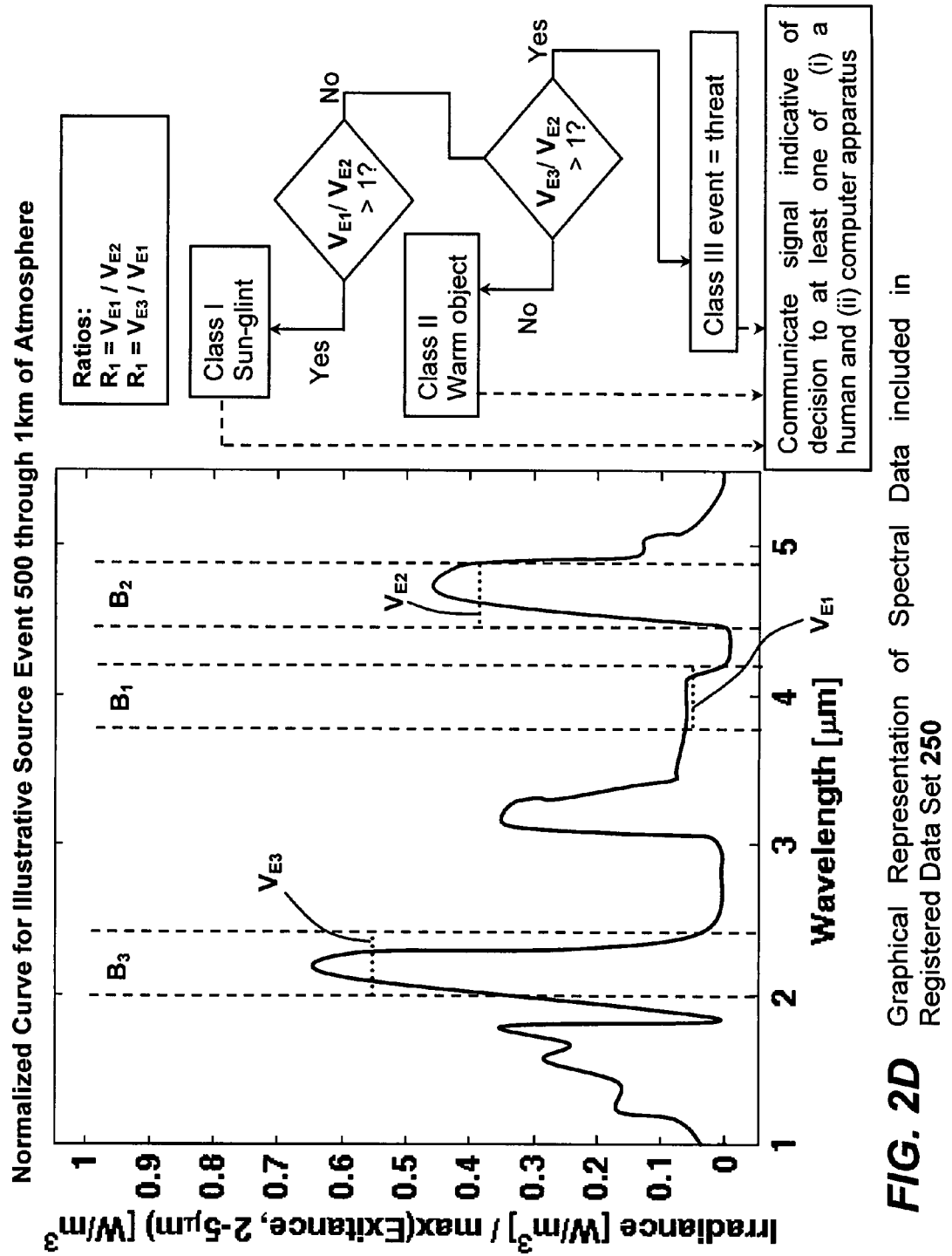
FIG. 2D Graphical Representation of Spectral Data included in Registered Data Set 250

Sheet 1 of 3 registering, at the spectral sensor, a spectral irradiance signature of the electromagnetic-energy emitting source event and storing a registered-data set indicative of the registered spectral irradiance signature in computer memory; 735 executing a spectral analysis algorithm that executes the steps of
(A) consulting the registered data set for the algorithmic analysis of at least first, second and third selected wavelength sub-ranges of the registered spectral irradiance signature represented by the registered-data set and associating with, respectively, the selected first, second and third wavelength sub-ranges, first, second and third relative-energy values, wherein each relative energy value corresponds to the intensity of energy registered at the spectral sensor within the wavelength sub-range with which that relative-energy value is associated;
(B) comparing to one another a first selected set of two of the relative-energy values;
(C) rendering a first class-eliminating determination that the emitting source event is not within a selected one of the first, second and third event classes based on whether a selected one of the relative-energy values included in the first selected set of two relative-energy values is one of (i) greater in magnitude and (ii) lesser in magnitude than the other of the relative-energy values included in the first selected set of two relative-energy values by at least a predetermined first threshold amount; and
(D) depending on the class that is eliminated through execution of the first class-eliminating determination, one of (i) terminating the analysis if, from the first class-eliminating determination, it is determined that the emitting source event conclusively belongs to a particular one of the first, second and third classes; and
(ii) if the first class-eliminating determination yields two remaining-candidate event classes, comparing to one another a second selected set of relative-energy values including the relative-energy value not selected for inclusion in the first selected set of two relative-energy values and one of the relative-energy values selected for inclusion in the first selected set of two relative-energy values, and rendering a second class-eliminating determination that the emitting source event is not within a selected one of the two remaining-candidate event classes based on whether a selected one of the relative-energy values included in the second selected set is one of (i) greater in magnitude and (ii) lesser in magnitude than the other of the relative-energy values included in the second selected set by at least a predetermined second threshold amount; and 755

| consulting, as a reference in the comparative analysis of the two energy values selected for inclusion in each class-eliminating determination, the modeled spectral data set is order to ascertain an expected ratio-comparative relationship as a function of at least both of (a) source-event type and (b) the selected wavelength sub-ranges; and (in some implementations)     765 |

↓

| measuring actual atmospheric conditions in the vicinity of the spectral sensor are and storing in computer memory a measured-conditions data set indicative of the measured conditions so as to facilitate the selection for reference in each class-eliminating determination the modeled spectral irradiance data having factored therein the atmospheric conditions most closely corresponding to the actual real-time atmospheric information.     745 |

SYSTEM AND METHOD FOR SPECTRAL-BASED PASSIVE THREAT WARNING

PROVISIONAL PRIORITY CLAIM

Priority based on Provisional Application Ser. No. 60/795,800, filed Apr. 28, 2006, and entitled "SYSTEM AND METHOD FOR SPECTRAL-BASED PASSIVE THREAT WARNING" is claimed. Moreover, the entirety of the previous provisional application, including the drawings, is incorporated herein by reference as if set forth fully in the present application.

BACKGROUND

Passive threat warning systems detect potential missile threats to aircraft and other assets by sensing emitted energy in the ultraviolet, visible, and/or infrared bands emitted from the suspected threat. These systems rely on spectral sensors and algorithms to discern actual threats from background clutter, for example. At present, infrared sensor technology as applied to a missile threat warning application implements a system wherein the energy emitted in one narrow band, or color, in the range of approximately 4.4 µm to 4.8 µm is compared to the energy emitted in another narrow band in the range of approximately 3.9 µm to 4.1 µm. Discernment between, for example, a so-called "sun glint" and an earthbound "hot object" or "hot event" such as a fire, a missile burn or a flamethrower is based upon the knowledge that the detectable energy associated with direct or reflected sunlight is markedly more intense in the 3.9 µm to 4.1 µm range than in the 4.4 µm to 4.8 µm range, while the emission spectrum of an earthbound "hot" or "warm" event is generally more intense in the 4.4 µm to 4.8 µm range than in the 3.9 µm to 4.1 µm range. Although such a "two-color sensor" facilitates the elimination from consideration as threats certain types of clutter sources (e.g., sun glints), current systems are generally incapable of further discerning whether an event not eliminated as clutter under the initial two-color regime presents an actual threat or whether, like direct or indirect sunlight, it is a benign energy emitter such as a warm factory smoke stack, a fire or a warm vehicle engine, for example. Accordingly, under current systems of threat discernment, numerous events not eliminated as sun-glint must be regarded as within the scope of potential threats to military assets and personnel, for example. This is problematic because personnel and non-human resources that could otherwise focus upon actual threats are instead assigned to at least the monitoring of benign events on the assumption that these events may present a threat. In still worse scenarios, ordnance may be expended in an attempt to neutralize an apparent threat. The unwarranted expenditure of ordinance amounts to waste and, furthermore, may (i) betray an otherwise secret position of personnel and assets and/or (ii) result in the unnecessary infliction of destruction and death.

Accordingly, there exists a need for a method and associated apparatus for discernment of threats that is more refined than that provided by, for example, a traditional "two-color" sensor and that can, more particularly, eliminate from consideration as apparent threats a larger scope of events with a greater degree of accuracy than previous discernment methods and devices.

SUMMARY

Variously implemented methods of discerning and classifying an electromagnetic-energy emitting source event include defining first, second and third classes of emitting source events. An illustrative schema of classification regards as first class events those events emitting electromagnetic energy the predominant source of which is of a non-terrestrial nature. Predominating the event sources categorized as first class (or class one) events is sunlight that is detected either directly or indirectly (reflected) at a predetermined location. The single largest source of non-terrestrial energy is the sun. Accordingly, included within the first event class are what have traditionally been referred to as sun-glints. Various classification schemas regard as second class events those terrestrial events that, while emitting a broadly energetic spectrum, are non-threatening. Second class events may include such sources as a running vehicle engine, a smoke stack emitting heated gases and particulate, a forest fire and metal heated by a welding torch, by way of non-limiting example. Second class events, under various schemas, may be regarded as so-called "warm" events. Third class events include terrestrial events that exhibit spectral characteristics associated with a predetermined set of recognized threats. For instance, burning missile exhaust, military aircraft exhaust and bomb explosions may be included among third class events. Third class events typically burn hotter than second class events and, therefore, may be regarded as "hot" events. Moreover, many events classified as class three events do not emit broadly over a large range of the electromagnetic spectrum and, accordingly, may have "gaps" in their emission spectra in which they do not emit at all. In various implementations, known gaps in the emission spectra of known threats are exploited in determining whether an unknown emitter exhibits characteristics consistent with a threat. For instance, certain "clean-burning" missiles do not emit at all at particular wavelengths within the range of, for instance, 3.5 to 4.27 microns. How a plume of burning missile-exhaust gases emits—which is not like a black body—is very much a function of the fuel burned to propel the missile.

An illustrative implementation includes providing reference-profile data indicative of an electromagnetic-irradiance profile associated with each model source-event of a selected set of model source events under a predetermined set of conditions including, by way of non-limiting example, selected atmospheric conditions and transmission distance. An illustrative electromagnetic-irradiance profile includes indications as to the relative intensity of remotely measurable energy (apparent intensity) at each wavelength of a selected set of wavelengths. A wavelength set within which to measure the relative intensity of detectable energy emitted from the emitting source is selected such that the selected wavelength set includes wavelengths for which irradiance behavior as a function of wavelength is represented in the reference-profile data. Selected from within the wavelength set are first, second and third electromagnetic-energy (wavelength) sub-ranges such that (i) each sub-range includes wavelengths whose average length is disparate from the average length of the wavelengths included in each of the other two sub-ranges, (ii) the average wavelength within each sub-range exhibits an irradiance disparate from the irradiances exhibited by the average wavelength of each of the other two sub-ranges, and (iii) each of the first, second and third sub-ranges includes at least one wavelength for which a relative irradiance is indicated in the reference-profile data. In various implementations, the sub-range selection is dependent, in part, on the types of events to be discerned and on the absorption characteristics of an atmosphere in which the method is to be implemented. On the one hand, selecting sub-ranges in which known events of interest exhibit distinct emission characteristics facilitates accuracy in classifying unknown events based on measurable emission (irradiance) spectra. On the other hand, regions of the electromagnetic spectrum from which the sub-ranges are selected should be selected with an understanding of the atmospheric-electromagnetic-energy absorption profile of the typical atmosphere in which a particular implementation is to be used. For instance, as is known to those of skill in the spectroscopy and spectral-imaging arts, earth's atmosphere manifests a so-called "dark-line" in the vicinity of 4.27 µm due to the presence of carbon dioxide ($CO_2$). Accordingly, a narrow sub-range centered on 4.27 µm would typically not yield sufficient spectral data to inform a discernment of event class. However, carefully-selected sub-ranges from either side of a dark line can be rich with spectral information due to the typically sharp upward slope in transmission of the atmosphere on either side of a dark line. Knowledge of the atmosphere in which a method of event-class discernment is implemented is important because the spectrum that a specified event actually emits differs from the measurable or apparent spectrum due to the absorption characteristics of the atmosphere, particularly when spectral measurements are registered by apparatus distant from the emitting source.

The relative intensity of detectable (i.e., measurable) energy emitted from the emitting source within each of the first, second and third energy sub-ranges is measured and first, second and third relative-energy values are associated with, respectively, the first, second and third energy sub-ranges, each relative-energy value corresponding to the intensity of energy measured (e.g., irradiance) in the energy sub-range with which that relative-energy value is associated. Each relative-energy value is typically representative of the average energy intensity registered in the sub-range with which it is associated. The relative-energy values of a first selected set of two of the three relative-energy values are compared to one another and, with reference to the reference-profile data, a first eliminating determination that the emitting source event is not within a selected one of the first, second and third event classes is rendered based on whether a selected one of the relative-energy values included in the first selected set of two relative-energy values is one of (i) greater in magnitude and (ii) lesser in magnitude than the other of the relative-energy values included in the first selected set of two relative-energy values by at least a predetermined first threshold amount. By eliminating as a candidate event class one of the three defined classes of event, the first eliminating determination yields two remaining-candidate event classes. For example, the first eliminating determination in various implementations is calculated to eliminate from the pool of candidate event classes non-terrestrial energy sources such as sun-glints. Accordingly, the first and second energy sub-ranges may be selected such that first class events (e.g., sun-light) exhibit a higher apparent (measurable) intensity in the first sub-range than in the second sub-range and second and third class events (e.g., terrestrial "warm" and "hot" events) exhibit a higher measurable intensity in the second sub-range than in the first sub-range. It will be appreciated, in connection with the illustrative example above, that an event from which the apparent energy is much more intense in the first sub-range than in the second sub-range may be regarded as a first class event and the analysis, in various implementations, may be terminated.

In various implementations in which the event is determined not to be an event of the first class, a class-elimination process continues by comparing to one another a second selected set of relative-energy values including the relative-energy value not selected for inclusion in the first selected set of two relative-energy values and one of the relative-energy values selected for inclusion in the first selected set of two relative-energy values. A second eliminating determination that the emitting source event is not within a selected one of the two remaining-candidate event classes is rendered based on consultation with the reference-profile data and on whether a selected one of the relative-energy values included in the second selected set is one of (i) greater in magnitude and (ii) lesser in magnitude than the other of the relative-energy values included in the second selected set by at least a predetermined second threshold amount. For example, continuing with the aforementioned hypothetical classification system in which a sun-glint is a first class event, warm events are second class events and hot events are third class events and, assuming the first eliminating determination indicates that the event under analysis is not a sun-glint based on a comparison between the first and second relative-energy values, then a determination needs to be rendered as to whether the event in question is a harmless warm event of (i.e., within) the second class or a threatening hot event of the third class.

Representative embodiments and implementations are more completely described in the following detailed description, the elucidation of which is facilitated by the schematic representations of, and numerical and graphical data relating to, an illustrative embodiment contained in the accompanying drawings.

BRIEF DESCRIPTION OF THE DRAWINGS

FIG. 2D is a graphical depiction of spectral data included in a registered data set associated with an illustrative source event to be classified by the system of FIG. 1.

DETAILED DESCRIPTION

The following description of a method and associated apparatus for classifying an electromagnetic-energy emitting source event is illustrative in nature and is therefore not intended to limit the scope of the invention or its application of uses. Accordingly, the various implementations, aspects, versions and embodiments described in the summary and detailed description are in the nature of non-limiting examples falling within the scope of the appended claims and do not serve to define the maximum scope of the claims.

Figure 1:
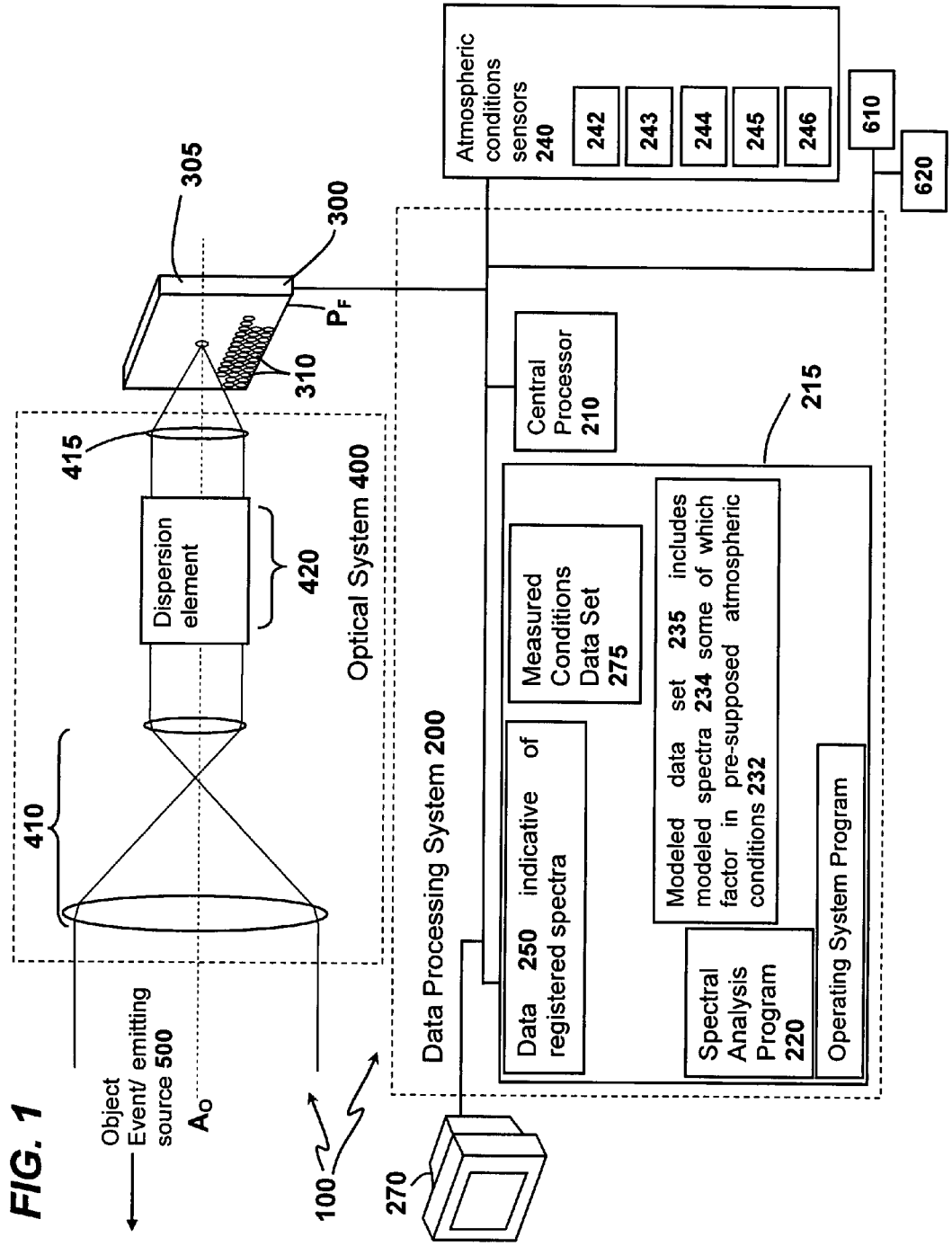
FIG. 1 schematically depicts the architecture of an illustrative spectral analysis system for classifying an electromagnetic-energy emitting source event.

Referring to FIG. 1, the architecture of an illustrative spectral analysis system 100 is schematically represented and includes (i) a data processing system 200; (ii) a spectral sensor 300 in the form of an imaging-sensor array 305 communicatively linked to the data processing system 200 and (iii) an optical system 400 configured for imaging electromagnetic energy emitted from an electromagnetic-energy emitting source 500 (hereinafter "energy source," "emitting source" or "source" 500) external to the optical system 400 onto the spectral sensor 300. The imaging-sensor array 305 may be alternatively referred to as the "detector array 305" in the current description and the claims appended hereto.

The data processing system 200 includes a central processor 210 and a memory device 215 and is programmed to execute spectral analysis algorithms 220 as described in more detail further in this description. Alternative implementations incorporate any of a variety of conventional imaging sensor arrays 305 adapted to detect wavelengths over a predetermined range of electromagnetic wavelengths and known to those in the relevant technical disciplines. A typical detector array 305 suitable for implementing embodiments of the invention includes photosensitive detectors elements 310 that are, to the extent practicable, uniformly sized and regularly spaced.

The optical system 400 schematically represented in the illustrative implementation of FIG. 1 includes a set of focusing elements 410 (e.g. a telescope) optically aligned with a set of optical dispersion apparatus 420 that may include one or more optically dispersive elements, for example. Located between the set of optical dispersion apparatus 420 and the spectral sensor 300 is a lens 415 situated such that the spectral sensor 300 corresponds in location to the focal plane $P_F$ of the lens 415. It is to be understood that numerous, alternatively configured optical systems 400 may be implemented in order to register spectral signatures at the spectral sensor 300 and that the particular optics chosen are immaterial, in a general sense, to various implementations. However, by way of non-limiting example, the set of optical dispersion apparatus 420 may alternatively include one or more of (i) a prism, (ii) a grism, and (iii) a grating. In one alternative embodiment, the optical system 400 includes plural lenses, each of which lenses includes an optical filter that passes only wavelengths of interest corresponding to a wavelength sub-region of interest. These lenses (not shown) would not be serially arranged in the optical train; they may, for instance, be arranged side-by-side and each would focus light of a specified wavelength range onto a dedicated portion of the detector array 305.

In conjunction with FIGS. 1 through 3, an illustrative method for classifying an electromagnetic-energy emitting source event as one of (i) a first class event, (ii) a second class event and (iii) a third class event, within a predetermined atmosphere exhibiting an atmospheric electromagnetic-absorption profile, is described below. Referring to FIG. 3, a sequence of method steps illustrates a method of classifying an electromagnetic-energy emitting source event. It is noted that the sequence of steps presented in the drawing and the text to follow is illustrative only and not necessarily indicative of the order in which the steps must be performed. Accordingly, nothing in the drawings, this description or the corresponding claims should be construed so as to limit the scope of the invention to a particular sequence of steps in the absence of explicit statements to the contrary or unless a particular order is inextricably dictated by context (e.g., an instance in which it is impossible to perform a particular step prior to the performance of another step). In addition, various alternative methods may not include all steps depicted or described. Moreover, although the particular apparatus used to execute method aspects is not relevant, reference is made to the illustrative apparatus of FIG. 1 in order to facilitate comprehension of the illustrative method.

As described previously in the background and summary, gases, particulates and water vapor present in an environment affect the transmission of electromagnetic energy through that environment. As a general observation, as distance from an energy emitting source is increased, the transmission of energy emitted from that source is decreased for any given wavelength in the emitted spectrum due to atmospheric absorption and scattering, for example. An atmosphere's electromagnetic-absorption profile is represented, for example, by an absorption spectrum in which a decrease in intensity of radiation at specific wavelengths or ranges of wavelengths characteristic of one or more absorbing substances in the atmosphere is manifested as a pattern of dark lines or bands. The effect of an atmosphere's absorption characteristics on the energy emitted from various illustrative emitters is illustrated in association with FIGS. 2A and 2B.

Figure 2A:
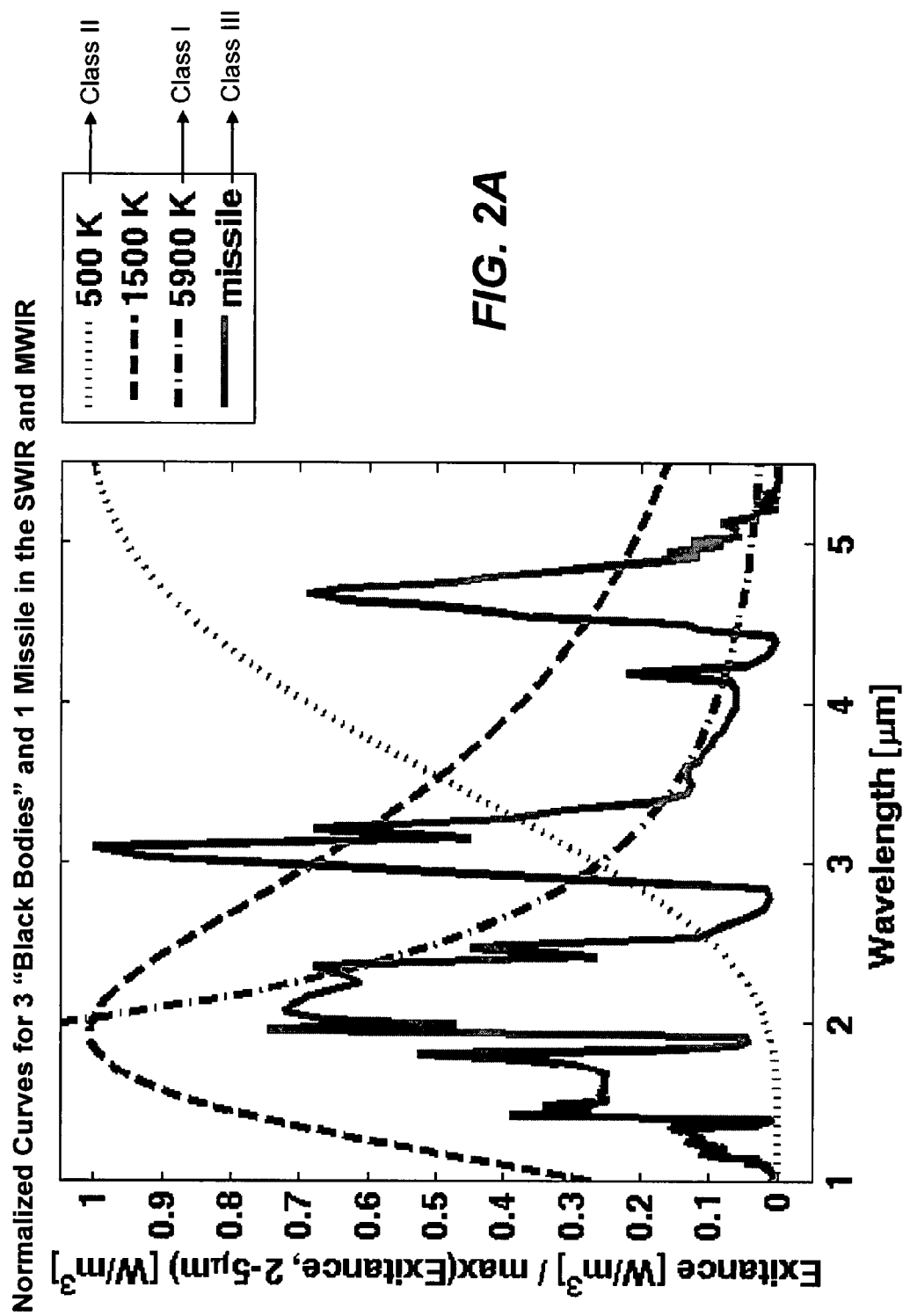
FIG. 2A is a graph including plots of normalized emittance for three black body emitters and an illustrative, non-black-body missile-exhaust burn.
Figure 2B:
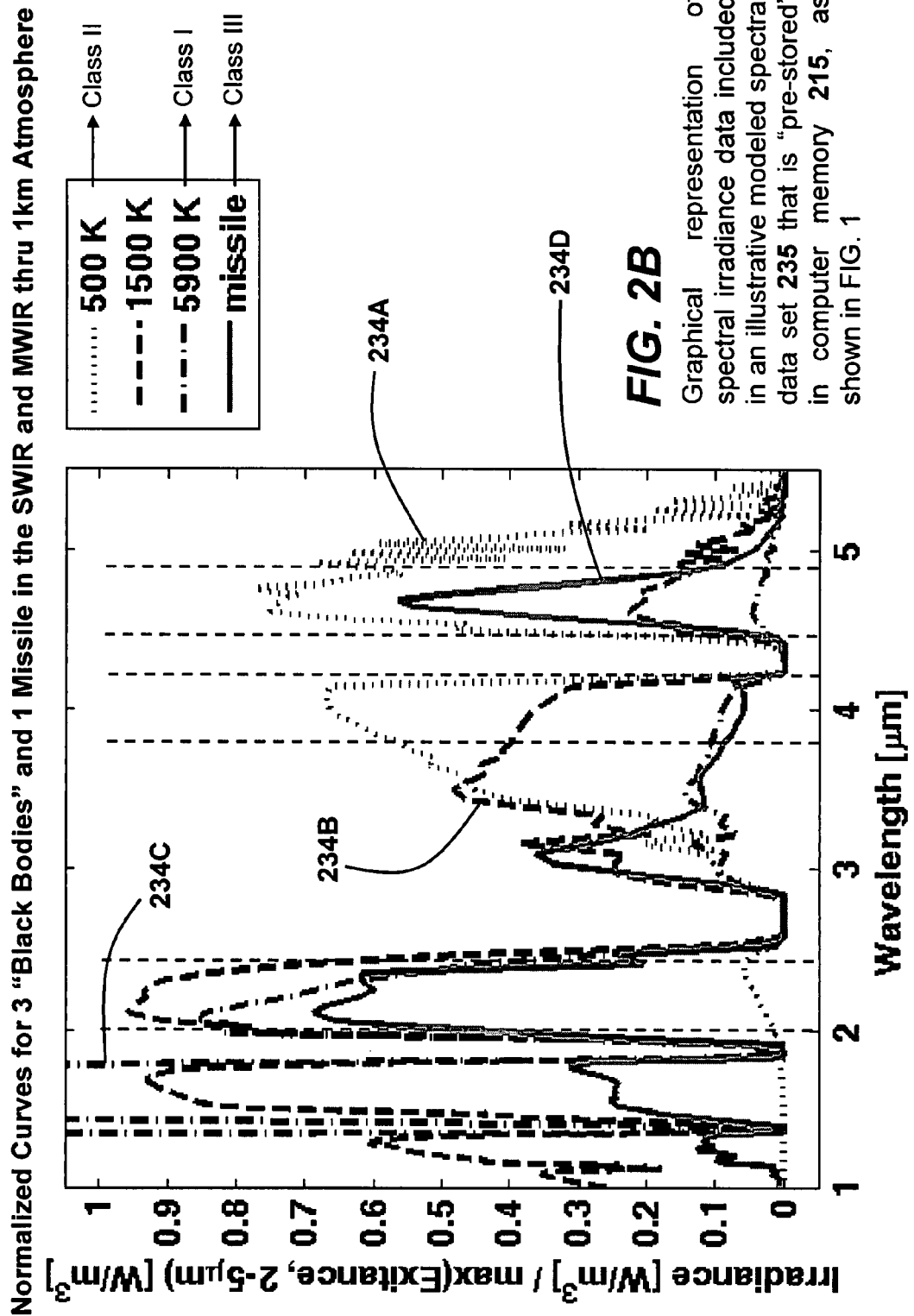
FIG. 2B is a graphically illustrates modeled normalized irradiance of the emitters whose emittances are plotted in FIG. 1 after transmission through 1 km of atmosphere under a predetermined set of atmospheric conditions.
Figure 3:
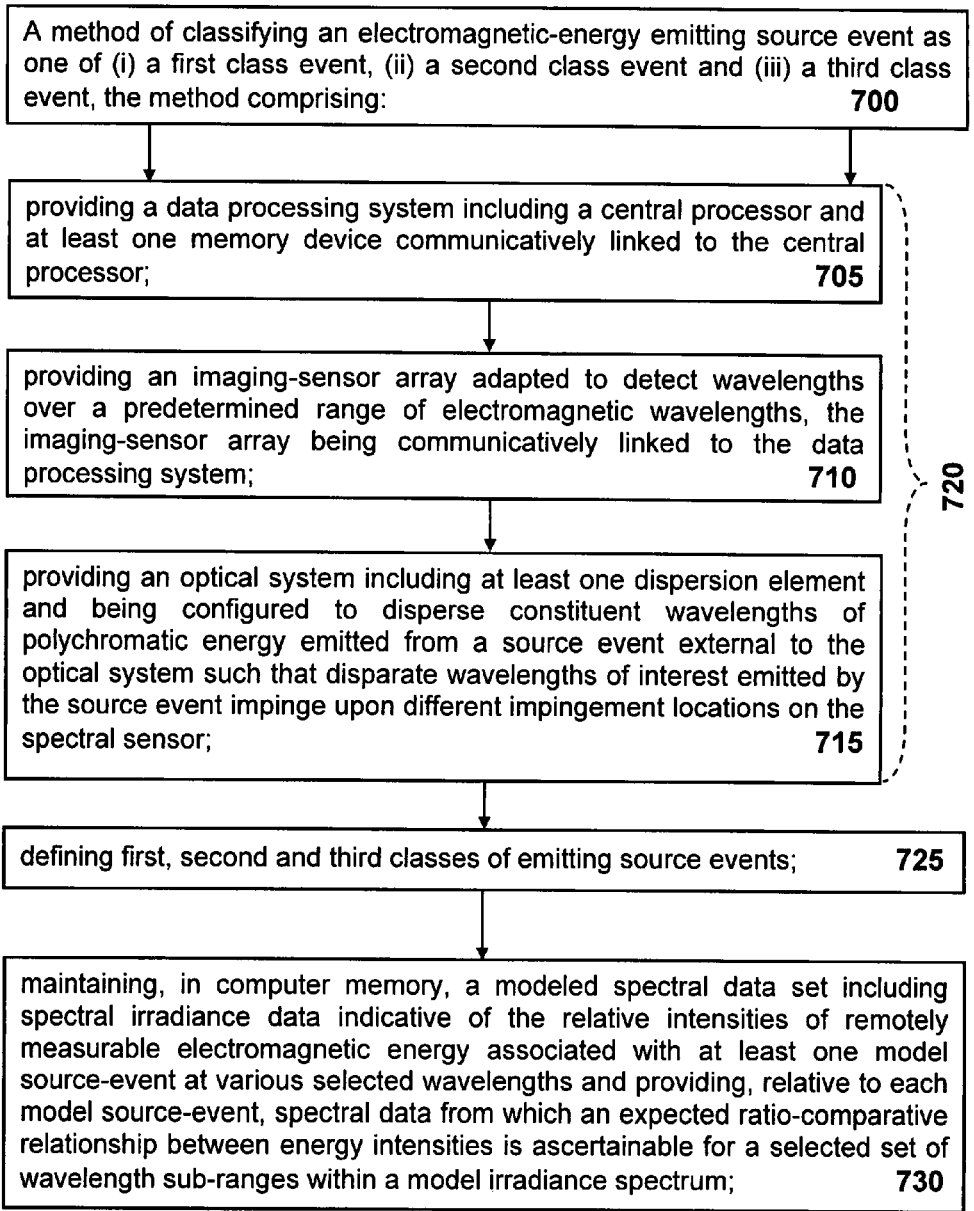
FIG. 3 depicts steps in an illustrative method for classifying an electromagnetic-energy emitting source event into one of three illustrative event classes.

FIG. 2A shows illustrative, normalized emission (exitance) curves for (i) the sun, which is treated as a black body emitter having a temperature of 5900° K, (ii) a warm object (e.g. a factory smoke stack), which is treated as a "warm" black body emitter at a temperature of 500° K, (iii) a hypothetical "hot" black body emitter at 1,500° K and (iv) an illustrative non-black-body plume of burning missile-exhaust gases, burning at 1,500K and including gaps in its emission spectrum over the wavelength range represented in the plots of FIG. 2A. The emission curves of FIG. 2A, which express emission in terms of individually normalized exitance as a function of wavelength for each of the previously described emitters, represent the various emission spectra in the absence of atmospheric absorption. By comparison, FIG. 2B is a graphical depiction showing plots of irradiance vs. wavelength for each of the emitters in FIG. 2A after the energy emitted therefrom has propagated a distance of 1 km through an illustrative atmosphere. The plots of FIG. 2B, in essence, indicate the "apparent" or "measurable" energy intensity of each emitter type at each of the wavelengths for which data is available. In addition to other "dark lines" resulting from atmospheric absorption, the carbon dioxide band in the vicinity of 4.27 μm (i.e., the $CO_2$ gap) is in evidence in the graph of FIG. 2B.

Referring now to FIG. 3, the illustrative method 700 includes a step 705 of providing a data processing system 200 including a central processor 210 and at least one memory device 215 communicatively linked to the processor.

At 710, a spectral sensor 300 adapted to detect wavelengths over a predetermined range of electromagnetic wavelengths in provided. The spectral sensor 300 is communicatively linked to the data processing system 200 in an operative manner that facilitates processing by the data processing system 200 of spectral data registered at the spectral sensor 300. An optical system 400 adapted for imaging electromagnetic energy emitted from an energy emitting source 500 external to the optical system onto the spectral sensor 300 is provided at step 715. In a typical embodiment, the optical system 400 disperses constituent wavelengths of the polychromatic energy emitted from source 500 so that disparate wavelengths of interest impinge upon different impingement locations on the spectral sensor 300. Accordingly, various implementations include at least one dispersion element 420 as described previously in association with the illustrative architecture of FIG. 1. It is to be understood that steps 705, 710 and 715 may be combined into a single step 720 of providing a spectral analysis system 100 including a data processing system, a spectral sensor 300 and an optically system 400 cooperatively arranged as generally described above.

Figure 2C:
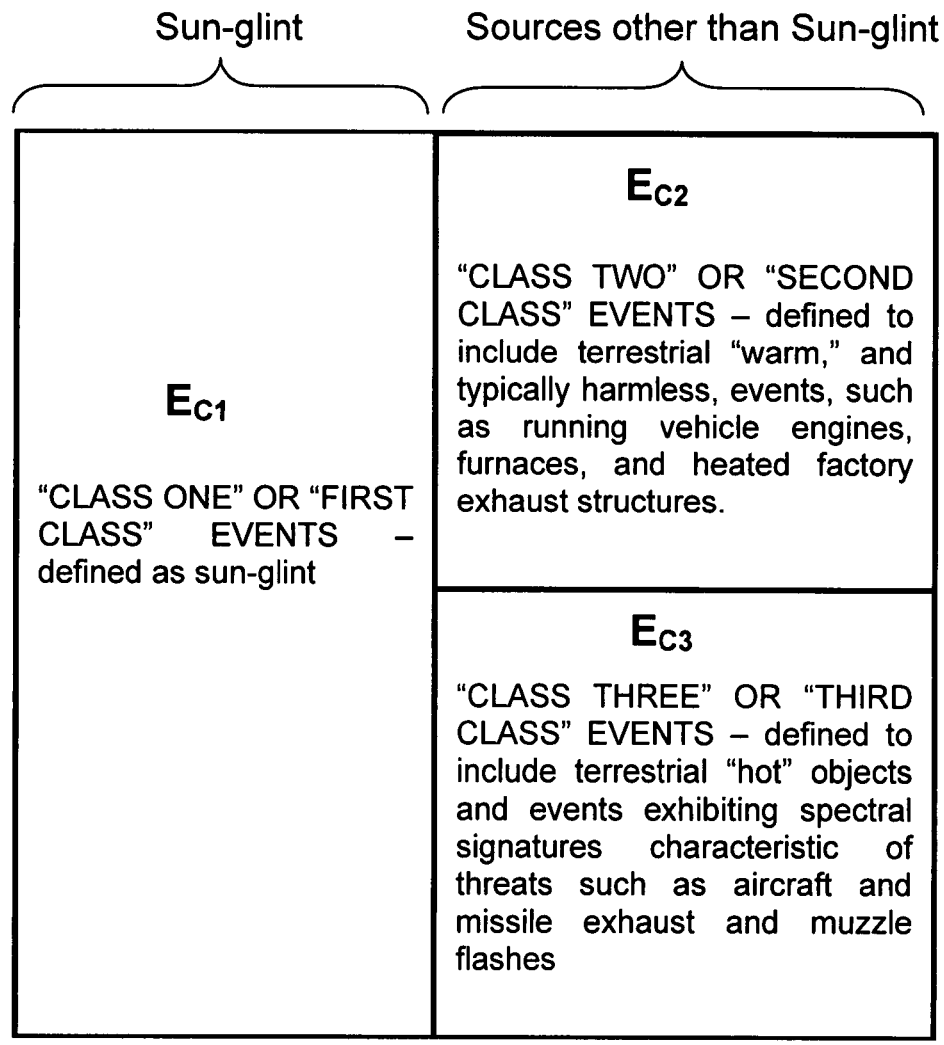
FIG. 2C is a diagram indicative of an illustrative "universe" of energetic events whose irradiance spectra implantations of the invention are configured to distinguish and identify.

Step 725 indicates defining first, second and third classes of emitting source events. Although, as previously discussed in the summary, the classes may be defined any number of ways, for purposes of illustration and comprehension, illustrative first, second and third classes are defined such that (i) a first class event is one whose primary source of emitted and remotely measurable energy is direct or indirect sun-light (e.g., a sun-glint), (ii) a second class event is one that is regarded as a non-threatening terrestrial event, which may also be referred to as a "warm" event, and (iii) a third class event is a terrestrial event exhibiting remotely-measurable spectral characteristics typically associated with recognized threats such as missiles. FIG. 2C is a diagram indicative of an illustrative "universe" of events consistent with the illustrative classification schema defined above. Moreover, in the plots of FIGS. 2A and 2B, the hypothetical first and second class events provided for illustrative purposes radiate like black bodies, while the curve of the illustrative, non-blackbody third class event includes various regions of low or zero irradiance or "apparent intensity" in its measurable emission spectrum (FIG. 2B). A comparison between the 1500K black body curve of FIG. 2B and the illustrative third class event, which also has a presupposed temperature of 1500K, indicates that at least a portion of the gap (or reduction) in remotely-measurable energy emission associated with the third class event is attributable to the nature of the non-blackbody emitting source (i.e., the source simply does not emit at all, or emits with very low relative intensity, along at least some of the wavelengths in the gap range), while the $CO_2$ dark line inherent in the atmosphere may account for a lack of detectable emission (e.g., irradiance) along at least another portion of the measurable-emission gap.

Referring to FIGS. 3 and 2B, step 730 indicates the maintenance (e.g., in computer memory 215) of a modeled source-event spectral data set 235 (FIG. 2B), which may be alternatively referred to hereinafter as "modeled spectral data set 235," "modeled-data set 235," or by some similar designation associated with reference number "235." For purposes of elucidating this aspect of the illustrative process, FIG. 2B includes a graphical representation of data pre-stored in an illustrative modeled-data set 235. The modeled-data set 235 includes spectral data indicative of the relative intensities (e.g. irradiance) of remotely measurable electromagnetic energy associated with at least one model source-event at various selected wavelengths. Relative to a particular model source-event, the modeled-data set 235 provides reference spectral data from which an expected ratio-comparative relationship between energy intensities is ascertainable for a selected set of wavelength sub-ranges within, for instance, a model irradiance spectrum, such as each of the illustrative model spectra 234a, 234b, 234c, and 234d depicted in FIG. 2B. Moreover, a typical implementation associates the reference spectral data associated with a model source-event with at least one pre-supposed transmission distance through at least one pre-contrived model atmosphere, each of which at least one model atmospheres associates with, and factors into, a model irradiance spectrum (e.g., any of 234a, 234b, 234c, and 234d) a predetermined set of atmospheric conditions 232. For instance, the four model spectra 234a, 234b, 234c, and 234d of FIG. 2B are modeled spectra for the model source-events to which they correspond at a distance of 1 km in an atmosphere in which the temperature range is between 50° F. and 75° F., the humidity is between 70% and 90%, the smog index is between X and Y and the pressure is between 758 and 762 mm of Hg.

In various implementations, it is useful to include within the modeled-data set 235, in association with each set of modeled atmospheric conditions, irradiance spectra for at least one model emitting event of each of the pre-defined first, second and third classes of event, as measured over the same transmission distance. For instance, as previously discussed, FIG. 2B represents the irradiance spectra for four different event-source types as measured (or modeled) at 1 km under the aforementioned atmospheric conditions. Providing modeled spectral data, such as that represented by the spectra 234A through 234D, for disparate event types provides a basis for ascertaining with improved certainty an expected ratio-comparative relationship as a function of source-event type and selected wavelength ranges, and, ultimately, a more accurate determination as to the event class into which an unknown event is properly categorized. For instance, consider, with reference to FIG. 2B, energy sub-ranges $B_1$, $B_2$ and $B_3$ and the modeled spectra 234C, 234A, and 234D corresponding with, respectively, class I, class II and class III events. Relative to a class I event, the energy intensity (e.g., average intensity) in the sub-range $B_1$ is greater than it is in the sub-range $B_2$. However, the opposite is true for both a class II and class III event; in each of these cases, the irradiance is higher in the second sub-range $B_2$ than it is in the first sub-range $B_1$. The aforesaid information alone provides a basis for rendering at least an initial determination as to whether a particular event is a class I event or either a class II or class III event. Class II and III events can be distinguished from one another by reference to the third sub-range $B_3$ and either of sub-ranges $B_1$ and $B_2$. More specifically, whereas irradiance within the third sub-range $B_3$ for a class II is lower than irradiance in either of the first and second sub-ranges $B_1$ and $B_2$ for a class II event, the opposite is true for a class III event; that is, for a class III event, irradiance is higher in the third energy sub-range $B_3$ than it is in either of the first and second energy sub-ranges $B_1$ and $B_2$ for a class III event. Depending on the energy sub-ranges selected, different ratio relationships may exist relative to a particular kind of event under a specified set of atmospheric conditions. However, in modeling events for subsequent reference in attempting to identify an unknown event, it is advantageous to select wavelength ranges such that, through a first ratio test in which intensity within one sub-range is compared to intensity within a second sub-range for each of two disparate model events representative of two event classes, one of the classes can be eliminated as a candidate class into which the unknown event falls. For instance, with reference to FIG. 2B, if an unknown event exhibits an irradiance spectrum for which irradiance is higher in sub-range $B_2$ than in sub-range $B_1$, it is determined that the unknown emitter is not a class I event. With advantageously selected sub-ranges, a second ration test facilitates a final determination into which of three classes an unknown emitting source event belongs. The details of such a determination are described subsequently in association with FIG. 2D and a hypothetical source event 500.

Step 735 prescribes registering, at the spectral sensor 300, a spectral signature of the electromagnetic-energy emitting source 500 and storing a registered-data set 250 indicative of the registered spectral signature in computer memory 215. FIG. 2D includes a graphical representation of such an illustrative registered-data set 250.

Various alternative versions include a step 745 according to which actual atmospheric conditions in the vicinity of the spectral sensor 300 are measured and a measured-conditions data set 275 indicative of the measured conditions is stored in computer memory 215. The measured conditions, in various implementations, correspond to those conditions factored into the data associated with at least one modeled spectrum (e.g., 234A, B, C or D) in the modeled-data set 235 and variously include, by way of non-limiting example, one or more of (i) temperature, (ii) humidity, (iii) smog (suspended-particulate) content, (iv) pressure and (v) altitude. Implementations accounting for actual atmospheric conditions are discussed in more detail in subsequent paragraphs of this detailed description. The "vicinity of the spectral sensor 300" may include, by way of non-limiting example, that portion of the atmosphere surrounding an aircraft by which the spectral analysis system 100 is carried.

At step 755, a spectral analysis algorithm (program 220, FIG. 1) is executed by the data processing system 200. The registered-data set 250 is consulted for the algorithmic analysis of at least first, second and third selected energy sub-ranges $B_1$, $B_2$ and $B_3$ of the registered spectral signature represented by the registered-data set 250. FIG. 2D graphically depicts an illustrative registered spectral signature and first, second and third selected energy sub-ranges $B_1$, $B_2$ and $B_3$ thereof, wherein the first illustrative sub-range $B_1$ extends from 3.8 μm to 4.2 μm, the second illustrative sub-range $B_2$ extends from 4.5 μm to 4.9 μm, and the third illustrative sub-range $B_3$ extends from 2.0 μm to 2.4 μm. Referring still to FIG. 2D, relative-energy values $V_{E1}$, $V_{E2}$ and $V_{E3}$ corresponding to the intensity of energy (e.g. average intensity, expressed in terms of normalized irradiance) registered at the spectral sensor 300 are assigned to, respectively, the first, second and third selected energy sub-ranges $B_1$, $B_2$ and $B_3$. In alternative implements, each of the relative-energy values $V_{E1}$, $V_{E2}$ and $V_{E3}$ may represent the maximum irradiance registered for any wavelength within each of the selected energy sub-ranges $B_1$, $B_2$ and $B_3$ or the area under the curve within each of the respective energy sub-ranges $B_1$, $B_2$ and $B_3$, by way of non-limiting example.

As described in the summary, the relative-energy values of a first selected set of two of the three relative-energy values $V_{E1}$, $V_{E2}$ and $E_{E3}$ of the sub-ranges $B_1$, $B_2$ and $B_3$ are algorithmically compared to one another and a first eliminating (class-eliminating) determination that the emitting source event in not within a selected one of the first, second and third event classes $E_{C1}$, $E_{C2}$ and $E_{C3}$ is rendered based on whether a selected one of the relative-energy values included in the first selected set of two relative-energy values is one of (i) greater in magnitude and (ii) lesser in magnitude than the other of the relative-energy values included in the first selected set of two relative-energy values by at least a predetermined first threshold amount. In the illustrative example associated with FIG. 2D, a first ratio $R_1$ relating the first energy value $V_{E1}$ to the second energy value $V_{E2}$ is computed. In this example, first and second energy sub-ranges $B_1$ and $B_2$ consistent with ranges analyzed in a typical traditional "two-color test" have been selected for ratio-comparative analysis of their corresponding energy values $V_{E1}$ and $V_{E2}$. More specifically, the first ratio $R_1$ in the present example is designed to facilitate a first eliminating determination in accordance with which a decision as to whether the source event is a sun-glint or something other than a sun-glint is rendered. Accordingly, the selected first and second energy sub-ranges $B_1$ and $B_2$ are on, respectively, the short-wavelength side and the long-wavelength side of the $CO_2$ atmospheric dark line manifest in the vicinity of 4.27 μm. Although the illustrative example of FIG. 2D shows the first energy value $V_{E1}$ as the numerator, and the second energy value $V_{E2}$ as the denominator, of the first ratio $R_1$, it will be appreciated that this is for illustrative purposes only and that, for example, the numerators and denominators could be reversed; the important aspect being that consistency is maintained in establishing ratios, making calculations and comparisons associated therewith, and rendering determinations based thereon. Moreover, any alternative selected ratios that represent equivalent mathematical and conceptual "truths" with respect to the registered data are to be regarded as literally the same expression and, therefore, within the literal scope of the claims. For instance, because the measured energy values are positive, a case in which stating that $V_{E1}/V_{E2}>1$ corresponds to a conclusion that the emitting source 500 is sun-glint is mathematically and conceptually equal to stating that $V_{E2}/V_{E1}<1$ corresponds to a conclusion that the emitting source 500 is sun-glint. Moreover, in various implementations in which a first eliminating determination is designed to differentiate between those events that are sun-glint and those events that are "something other than sun-glint," either of the immediately aforesaid ratio-based conclusions is equivalent to stating either of (i) $V_{E1}/V_{E2}<1$ and (ii) $V_{E2}/V_{E1}>1$ corresponds to a conclusion that the emitting source 500 is something other than sun-glint. In any event, regardless of how the first ratio $R_1$ and the conclusion to be rendered therefrom are defined in any particular implementation, a comparison between a selected two of the three relative-energy values $V_{E1}$, $V_{E2}$ and $E_{E3}$ serves as the basis for rendering a first eliminating determination that, in an implementation in which all possible events fall into one of three event classes, either (i) reduces the number of remaining candidate classes to two or (ii) serves as the basis for terminating the analysis if, for example, it is determined, based on the first eliminating determination, that the emitting source presents no threat (e.g., it is conclusively sun-glint).

In rendering a first eliminating determination, a precontrived, modeled spectral data set 235 (e.g., FIG. 2B) is consulted in accordance with step 765 as a reference in the comparative analysis of the two energy values selected for inclusion in the first ratio $R_1$. As previously explained, the modeled spectral data 235 stored in memory 215 provides a basis for ascertaining an expected ratio-comparative relationship between relative-energy values as a function of at least both of (i) source-event type (e.g., $E_{C1}$, $E_{C2}$ or $E_{C3}$) and (ii) the selected set of energy sub-ranges (e.g., $B_1$ and $B_2$). A specific illustrative example is now provided in conjunction with FIGS. 2D and 2B. Referring to the registered spectral data of FIG. 2D, the first energy value $V_{E1}$ associated with the first energy sub-range $B_1$ is lesser in magnitude than the second energy value $V_{E2}$ associated with the second energy sub-range $B_2$ (i.e., $V_{E1}<V_{E2}$ or $V_{E1}/V_{E2}<1$). Reference to the modeled spectral data 235 of FIG. 2B indicates, for the corresponding energy sub-ranges $B_1$ and $B_2$, that when $V_{E1}<V_{E2}$, the emitting source event 500 is not an emitter that emits like sun-glint. In other words, $V_{E1}/V_{E2}<1$ is not an "expected ratio behavior" corresponding to sun-glints for the selected sub-ranges $B_1$ and $B_2$. Accordingly, for this example, a first eliminating determination indicating that the source event is not sun-glint, a class one event, is rendered as illustrated by the decision-chart portion of FIG. 2D. Moreover, the first eliminating determination has reduced the candidate event classes to classes two and three.

In order to discern whether a class two or three event issued the distally-registered spectrum, a second comparative relationship between the previously non-selected energy value (i.e., $V_{E3}$) and one of the two energy values, $V_{E1}$, and $V_{E2}$, previously selected for comparison is made. Which of the two previously selected values is selected for comparison with the previously non-selected energy value will, in general, vary among implementations and circumstances. However, for purposes of description and explanation in connection with the present example, the third energy value $V_{E3}$ is compared to the second energy value $V_{E2}$. Reference to FIG. 2D indicates that the third energy value $V_{E3}$ associated with the third energy sub-range $B_3$ is greater in value than the second energy value $V_{E2}$ associated with the second energy sub-range $B_2$ (i.e., $V_{E3}>V_{E2}$ or $V_{E3}/V_{E2}>1$). Reference to the modeled spectral data 235 of FIG. 2B indicates, for the corresponding energy sub-ranges $B_3$ and $B_2$, that when $V_{E3}>V_{E2}$, the emitting source event 500 is not an emitter that emits like a class two, terrestrial "warm" source. In other words, $V_{E3}/V_{E2}>1$ is not an "expected ratio behavior" corresponding to typically-harmless warm events for the selected sub-ranges $B_3$ and $B_2$. Accordingly, for this example, a second eliminating determination indicating that the source event is not a class two event is rendered. Accordingly, the second eliminating determination has reduced the candidate event classes to class three only and a determination is rendered indicating that the spectrum-issuing source event 500 is a third class event and, therefore, is to be regarded a threat.

In various alternative implementations, a signal indicative of the outcome of each algorithmic class-eliminating determination is communicated to at least one of (i) a human being and (ii) computer apparatus in order to facilitate appropriate responsive action. For instance, a first eliminating determination resulting in a conclusion that the spectrum-issuing source event 500 is sun-glint may yield, in addition to an instruction to the data processing system 200 to terminate the algorithmic analysis, a signal or instruction to communicate to a human being (e.g. a pilot or threat-monitoring member of the military) at least one of an (i) audible and (ii) visible indicium indicative of the benign nature of the source event 500. For example, the data processing system 200 may cause to be displayed upon a monitor 270 (FIG. 1) a visible signal that the source event 500 presents no threat. Analogously, when a final algorithmic eliminating determination indicates that the spectrum-issuing source event 500 is to be regard as a threat, a signal indicative of this outcome is, in various implementations, communicated to at least one of (i) a human being and (ii) computer apparatus in order to facilitate appropriate responsive action. For instance, a computer monitor 270 may display at least a signal, if not other relevant data such as location of the source event 500, to a human (not shown) who is in a position to either initiate a response or instruct others to respond. Illustrative responses may include, by way of non-limiting example, at least one of (i) evasive maneuvers, (ii) the deployment of decoys to attract, for example, a missile and (iii) the issuance of ordinance directed at the spectrum-issuing source event 500 or the location from which the source event 500 originated. In still additional versions, a signal may be communicated to at least one of (i) an automated weapons system 600 for the automated issuance of ordinance and (ii) an automated vehicle maneuvering system 620 (e.g., "autopilot") capable of assisting a vehicle (e.g. aircraft) by which the system 620 is carried in evading an incoming threat.

As discussed at some length in the summary, and in the detailed description, some implementations of system 100 facilitate the acquisition and use of actual "real-time" atmospheric information. Accordingly, with reference to FIG. 1, various implementations include a set of atmospheric-condition sensors 240 for measuring atmospheric conditions and additional method steps are included for rendering the spectral analysis system 100 adaptable for use under a greater variety of conditions. The atmospheric-condition sensors 240 are communicatively linked to the data processing system 200 in order to facilitate the storage in computer memory 215 of their outputs. Illustrative, non-limiting examples of atmospheric-condition sensors 240 variably associated with alternative implementations include, as shown in FIG. 1, (i) a temperature sensor 242, (ii) a humidity sensor 243, (iii) a pressure sensor 244, (iv) an to altimeter 245 and (v) a nephelometer 246, or other instrument, for measuring the gaseous and suspended-particulate (aerosol) characteristics of the relevant atmosphere. Atmospheric data registered by at least one atmospheric-conditions sensor 240 is stored as, or in association with, a registered (or measured) conditions data set 275. The association of real-time atmospheric information with the registration, at the spectral sensor 300, of a spectral irradiance signature from source event 500 facilitates the selection for reference in each class-eliminating determination the model irradiance spectrum (from the modeled-data set 235) having factored therein the atmospheric conditions most closely corresponding to the actual real-time atmospheric information.

The foregoing is considered to be illustrative of the principles of the invention. Furthermore, since modifications and changes to various aspects and implementations will occur to those skilled in the art without departing from the scope and spirit of the invention, it is to be understood that the foregoing does not limit the invention as expressed in the appended claims to the exact construction, implementations and versions shown and described.

What is claimed is:

1. A method of classifying an electromagnetic-energy emitting source event as one of (i) a first class event, (ii) a second class event and (iii) a third class event, the method comprising:
   selecting first, second and third electromagnetic-energy sub-ranges such that each sub-range includes wavelengths whose average length is disparate from the average length of the wavelengths included in each of the other two sub-ranges;
   defining first, second and third classes of emitting source events;
   measuring the relative intensity of detectable energy emitted from the emitting source event within each of the first, second and third energy sub-ranges and associating with, respectively, the first, second and third energy sub-ranges, first, second and third relative-energy values, each relative-energy value corresponding to the intensity of energy measured in the energy sub-range with which that relative-energy value is associated;
   comparing to one another a first selected set of two of the relative-energy values and rendering a first eliminating determination that the emitting source event is not within a selected one of the first, second and third event classes based on whether a selected one of the relative-energy values included in the first selected set of two relative-energy values is one of (i) greater in magnitude and (ii) lesser in magnitude than the other of the relative-energy values included in the first selected set of two relative-energy values by at least a predetermined first threshold amount, the first eliminating determination yielding two remaining-candidate event classes; and
   comparing to one another a second selected set of relative-energy values including the relative-energy value not selected for inclusion in the first selected set of two relative-energy values and one of the relative-energy values selected for inclusion in the first selected set of two relative-energy values, and rendering a second eliminating determination that the emitting source event is not within a selected one of the two remaining-candidate event classes based on whether a selected one of the relative-energy values included in the second selected set is one of (i) greater in magnitude and (ii) lesser in magnitude than the other of the relative-energy values included in the second selected set by at least a predetermined second threshold amount.

2. The method claim 1 wherein
   (i) the average of the wavelengths selected for inclusion in the first sub-range is greater than 3.0 microns and less than 4.27 microns;

(ii) the average of the wavelengths selected for inclusion in the second sub-range is greater than 4.27 microns and less than 5.5 microns; and (iii) the average of the wavelengths selected for inclusion in the third sub-range is less than 3.0 microns.

3. The method of claim 2 wherein, within a predetermined atmosphere exhibiting an atmospheric electromagnetic-absorption profile, the energy sub-ranges are selected, and the event classes are defined, such that (i) the measurable energy of a first class event is more intense in the first energy sub-range than in the second energy sub-range;

(ii) the measurable energy of each of a second class event and a third class event is more intense in the second energy sub-range than in the first energy sub-range;

(iii) the measurable energy of second class event is less intense in the third energy sub-range than in each of the first and second energy sub-ranges; and (iv) the measurable energy of a third class event is more intense in the third energy sub-range than in at least one of the first and second energy sub-ranges.

4. The method of claim 3 wherein (i) a first class event includes one of (a) direct and (b) reflected sunlight;

(ii) a second class event is a terrestrial event that is regarded as non-threatening; and (iii) a third class event is a terrestrial event that exhibits a measurable spectrum characteristic of a threatening event.

5. The method of claim 3 wherein (i) a first class event includes one of (a) direct and (b) reflected sunlight;

(ii) a second class event is a terrestrial event that is regarded as non-threatening; and (iii) a third class event is a terrestrial event that exhibits a measurable spectrum characteristic of a threatening event.

6. A method of classifying an electromagnetic-energy emitting source event as one of (i) a first class event, (ii) a second class event and (iii) a third class event, the method comprising:

providing a data processing system including a central processor and at least one memory device communicatively linked to the central processor;

providing a spectral sensor and communicatively linking the spectral sensor to the data processing system, the spectral sensor being adapted to detect electromagnetic wavelengths over a predetermined wavelength range;

providing an optical system including at least one dispersion element and being configured to disperse constituent wavelengths of polychromatic energy emitted from a source event external to the optical system such that disparate wavelengths of interest emitted by the source event impinge upon different impingement locations on the spectral sensor;

defining first, second and third classes of emitting source events;

maintaining, in computer memory, a modeled spectral data set including spectral irradiance data indicative of the relative intensities of remotely measurable electromagnetic energy associated with at least one model source-event at various selected wavelengths and providing, relative to each model source-event, spectral data from which an expected ratio-comparative relationship between energy intensities is ascertainable for a selected set of wavelength sub-ranges within a model irradiance spectrum;

registering, at the spectral sensor, a spectral irradiance signature of the electromagnetic-energy emitting source event and storing a registered-data set indicative of the registered spectral irradiance signature in computer memory;

consulting the registered data set for the algorithmic analysis of at least first, second and third selected wavelength sub-ranges of the registered spectral irradiance signature represented by the registered-data set and associating with, respectively, the selected first, second and third wavelength sub-ranges, first, second and third relative-energy values, wherein each relative energy value corresponds to the intensity of energy registered at the spectral sensor within the wavelength sub-range with which that relative-energy value is associated;

comparing to one another a first selected set of two of the relative-energy values;

rendering a first class-eliminating determination that the emitting source event is not within a selected one of the first, second and third event classes based on whether a selected one of the relative-energy values included in the first selected set of two relative-energy values is one of (i) greater in magnitude and (ii) lesser in magnitude than the other of the relative-energy values included in the first selected set of two relative-energy values by at least a predetermined first threshold amount; and depending on the class that is eliminated through execution of the first class-eliminating determination, one of (i) terminating the analysis if, from the first class-eliminating determination, it is determined that the emitting source event conclusively belongs to a particular one of the first, second and third classes; and (ii) if the first class-eliminating determination yields two remaining-candidate event classes, comparing to one another a second selected set of relative-energy values including the relative-energy value not selected for inclusion in the first selected set of two relative-energy values and one of the relative-energy values selected for inclusion in the first selected set of two relative-energy values, and rendering a second class-eliminating determination that the emitting source event is not within a selected one of the two remaining-candidate event classes based on whether a selected one of the relative-energy values included in the second selected set is one of (i) greater in magnitude and (ii) lesser in magnitude than the other of the relative-energy values included in the second selected set by at least a predetermined second threshold amount; wherein (i) each class-eliminating determination is furthermore based upon consultation with the modeled spectral data set in order to ascertain an expected ratio-comparative relationship as a function of at least both of (a) source-event type and (b) the selected wavelength sub-ranges; and (ii) a signal indicative of the outcome of each class-eliminating determination is communicated to at least one of (a) a human being and (b) computer apparatus in order to facilitate appropriate responsive action.

7. The method claim 6 wherein (i) the average of the wavelengths selected for inclusion in the first sub-range is greater than 3.0 microns and less than 4.27 microns;

(ii) the average of the wavelengths selected for inclusion in the second sub-range is greater than 4.27 microns and less than 5.5 microns; and (iii) the average of the wavelengths selected for inclusion in the third sub-range is less than 3.0 microns.

8. The method of claim 7 wherein, within a predetermined atmosphere exhibiting an atmospheric electromagnetic-absorption profile, the energy sub-ranges are selected, and the event classes are defined, such that
  (i) the measurable energy of a first class event is more intense in the first energy sub-range than in the second energy sub-range;
  (ii) the measurable energy of each of a second class event and a third class event is more intense in the second energy sub-range than in the first energy sub-range;
  (iii) the measurable energy of second class event is less intense in the third energy sub-range than in each of the first and second energy sub-ranges; and
  (iv) the measurable energy of a third class event is more intense in the third energy sub-range than in at least one of the first and second energy sub-ranges.

9. The method of claim 8 wherein
  (i) a first class event includes one of (a) direct and (b) reflected sunlight;
  (ii) a second class event is a terrestrial event that is regarded as non-threatening; and
  (iii) a third class event is a terrestrial event that exhibits a measurable spectrum characteristic of a threatening event.

10. The method of claim 7 wherein
  (i) a first class event includes one of (a) direct and (b) reflected sunlight;
  (ii) a second class event is a terrestrial event that is regarded as non-threatening; and
  (iii) a third class event is a terrestrial event that exhibits a measurable spectrum characteristic of a threatening event.

11. The method of classifying an electromagnetic-energy emitting source event of claim 6 wherein
  (a) factored into the modeled spectral data associated with each model source-event of a selected set of modeled source events in the modeled spectral data set is a predetermined set of atmospheric conditions; and
  (b) the data processor is communicatively linked to a set of atmospheric-condition sensors capable of acquiring and communicating to computer memory, in association with the registration at the spectral sensor of a spectral irradiance signature of the electromagnetic-energy emitting source event, a registered conditions data set indicative of actual real-time atmospheric information, thereby facilitating the selection for reference in each class-eliminating determination the modeled spectral irradiance data having factored therein the atmospheric conditions most closely corresponding to the actual real-time atmospheric information.

12. The method of claim 11 wherein the set of atmospheric-condition sensors includes at least one of
  (i) a temperature sensor;
  (ii) a humidity sensor;
  (iii) a pressure sensor;
  (iv) an altimeter; and
  (v) a sensor for measuring gaseous and suspend-particulate content.

13. The method of claim 12 wherein
  (i) a first class event includes one of (a) direct and (b) reflected sunlight;
  (ii) a second class event is a terrestrial event that is regarded as non-threatening; and
  (iii) a third class event is a terrestrial event that exhibits a measurable spectrum characteristic of a threatening event.

14. The method of claim 13 wherein, within a predetermined atmosphere exhibiting an atmospheric electromagnetic-absorption profile, the energy sub-ranges are selected, and the event classes are defined, such that
  (i) the measurable energy of a first class event is more intense in the first energy sub-range than in the second energy sub-range;
  (ii) the measurable energy of each of a second class event and a third class event is more intense in the second energy sub-range than in the first energy sub-range;
  (iii) the measurable energy of second class event is less intense in the third energy sub-range than in each of the first and second energy sub-ranges; and
  (iv) the measurable energy of a third class event is more intense in the third energy sub-range than in at least one of the first and second energy sub-ranges.

15. The method claim 14 wherein
  (i) the average of the wavelengths selected for inclusion in the first sub-range is greater than 3.0 microns and less than 4.27 microns;
  (ii) the average of the wavelengths selected for inclusion in the second sub-range is greater than 4.27 microns and less than 5.5 microns; and
  (iii) the average of the wavelengths selected for inclusion in the third sub-range is less than 3.0 microns.

* * * * *